United States Patent
Itskovich et al.

(10) Patent No.: US 6,429,654 B1
(45) Date of Patent: *Aug. 6, 2002

(54) NUCLEAR MAGNETIC RESONANCE PULSE SEQUENCE FOR IMPROVING SIGNAL-TO-NOISE RATIO

(75) Inventors: Gregory Itskovich; Arcady Reiderman, both of Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/672,413

(22) Filed: Sep. 28, 2000

Related U.S. Application Data

(63) Continuation-in-part of application No. 09/151,871, filed on Sep. 11, 1998, now Pat. No. 6,163,153.

(51) Int. Cl.[7] .................................................. G01V 3/00
(52) U.S. Cl. ...................................... 324/314; 324/303
(58) Field of Search ................................ 324/303, 314, 324/307, 300, 309, 320–322

(56) References Cited

U.S. PATENT DOCUMENTS

| | | | | |
|---|---|---|---|---|
| 4,318,043 A | | 3/1982 | Crooks et al. | 324/309 |
| 5,023,551 A | * | 6/1991 | Kleinberg et al. | 324/303 |
| 5,212,448 A | | 5/1993 | De Roux et al. | 324/309 |
| 5,451,873 A | | 9/1995 | Freedman et al. | 324/303 |
| 5,796,252 A | * | 8/1998 | Kleinberg et al. | 324/303 |
| 5,910,112 A | | 6/1999 | Judd et al. | 600/410 |
| 6,005,389 A | | 12/1999 | Prammer | 324/303 |
| 6,163,153 A | * | 12/2000 | Reiderman et al. | 324/314 |

* cited by examiner

*Primary Examiner*—Edward Lefkowitz
*Assistant Examiner*—Tiffany A. Fetzner
(74) *Attorney, Agent, or Firm*—Madan, Mossman & Sriram, P.C.

(57) ABSTRACT

A method for acquiring nuclear magnetic resonance measurements of a material uses a gradient tool. A modified CPMG sequence is used wherein the duration of the refocusing pulse is selected to maximize the SNR of the pulse echoes relative to a standard CPMG sequence in which the refocusing pulse has twice the duration of the tipping pulse.

3 Claims, 8 Drawing Sheets

NUCLEAR MAGNETIC RESONANCE PULSE SEQUENCE FOR IMPROVING SIGNAL-TO-NOISE RATIO

CROSS-REFERENCES TO RELATED APPLICATIONS

This application is a continuation-in-part of U.S. patent application Ser. No. 09/151,871, filed on Sep. 11, 1998, now U.S. Pat. 6,163,153 issued on Dec. 19, 2000.

BACKGROUND OF THE INVENTION

1. Field of the Invention

The invention is related to the field of nuclear magnetic resonance ("NMR") apparatus and methods. More specifically, the invention is related to methods for conducting NMR measurements in a manner which optimizes the use of electrical power by the NMR instrument.

2. Description of the Related Art

NMR instruments adapted for well logging can be used for determining, among other things, the fractional volume of pore space and the fractional volume of mobile fluid filling the pore space of earth formations. Methods for using NMR well logging measurements for determining the fractional volume of pore space and the fractional volume of mobile fluids are described, for example, in, *Spin Echo Magnetic Resonance Logging: Porosity and Free Fluid Index Determination*, M. N. Miller et al, Society of Petroleum Engineers paper no. 20561, Richardson, Tex. (1990).

NMR well logging instruments known in the art are typically designed to make measurements corresponding to an amount of time for hydrogen nuclei present in the earth formation to realign their spin axes, and consequently their bulk magnetization, either with an externally applied static magnetic field, or perpendicularly to the magnetic field, after momentary reorientation of the nuclear spin axes. The externally applied magnetic field is typically provided by a permanent magnet disposed in the NMR instrument. The spin axes of the hydrogen nuclei in the earth formation, in the aggregate, become aligned with the static magnetic field induced in the earth formation by the permanent magnet. The NMR instrument also includes an antenna positioned near the magnet and shaped so that a pulse of radio frequency (RF) power conducted through the antenna induces a corresponding RF magnetic field in the earth formation in a direction orthogonal to the static field induced by the permanent magnet. This RF pulse (called an "A-pulse" hereafter) has a duration and amplitude selected so that the spin axes of the hydrogen nuclei generally align themselves perpendicular both to the RF magnetic field and to the static magnetic field. After the A-pulse ends, the nuclear magnetic moment of the hydrogen nuclei gradually "relax" or return to their alignment with the static magnetic field. The amount of time taken for this relaxation is related to the properties of interest of the earth formation.

Also after the A-pulse ends, the antenna is typically electrically connected to a receiver, which detects and measures voltages induced in the antenna by precessional rotation of the spin axes of the hydrogen nuclei. While the hydrogen nuclei gradually realign their spin axes with the static magnetic field, they do so at different rates because of inhomogeneities in the magnet's field and because of differences in the chemical and magnetic environment within the earth formation. Different rates of realignment of the spin axes of the hydrogen nuclei result in a rapid decrease in the voltage induced in the antenna. The rapid decrease in the induced voltage is referred to as the free induction decay (FID).

After a predetermined time period following the FID, another, longer RF pulse (called a "B-pulse" hereafter) is applied to the antenna. The B-pulse has a duration and amplitude selected to reorient the spin axes of the hydrogen nuclei in the earth formation by an axial rotation of 1800 from their immediately previous orientations. After the B-pulse, hydrogen nuclear spin axes that were realigning with the externally applied field at a slower rate then are positioned so that they are "ahead" of the faster realigning nuclear spin axes. This causes the faster realigning axes to be positioned "behind" the slower realigning spin axes. The faster realigning spin axes then eventually "catch up" to, and come into approximate alignment with, the slower aligning spin axes at some time after the B-pulse. As a large number of the spin axes become aligned with each other, the hydrogen nuclei again are able to induce measurable voltages in the antenna. The voltages induced as a result of realignment of the hydrogen nuclear spin axes with each other after a B-pulse is referred to as a "spin echo". The voltage induced by the spin echo is typically smaller than the original FID voltage induced after cessation of the A-pulse, because the aggregate nuclear axial alignment, and consequently the bulk magnetization, of the hydrogen nuclei at the time of the spin echo is at least partially realigned with the static magnetic field and away from the sensitive axis of the antenna. The spin echo voltage itself rapidly decays by FID as the faster aligning nuclear axes again "dephase" from the slower aligning nuclear axes.

After another period of time equal to two of the predetermined time periods between the A-pulse and the first B-pulse, another B-pulse of the same amplitude and duration as the first B-pulse can be applied to the antenna. This next B-pulse again causes the slower realigning spin axes to be positioned ahead of the faster realigning axes, and eventually another spin echo will induce voltages in the antenna. The voltages induced by this next spin echo will typically be smaller those induced by the previous spin echo.

Successive B-pulses are applied at regular time intervals to the antenna to generate successive spin echoes, each one typically having a smaller amplitude than the previous spin echo. The rate at which the peak amplitude of the spin echoes decreases is related to the properties of interest of the earth formation, such as the fractional volume of pore space or the fractional volume of mobile fluid filling the pore space. The number of spin echoes needed to determine the rate of spin echo amplitude decay is related to the properties of the earth formation. In some cases as many as 1,000 spin echoes may be needed to determine the amplitude decay corresponding to the particular formation properties of interest.

A limitation of NMR well logging instruments using the just-described RF pulse sequence is that this pulse sequence uses a very large amount of electrical power. Typically the DC power requirement for the NMR logging instruments known in the art is about 1 KW; the peak power required for effective nuclear excitation can be as high as 30 KW in each pulse. As is known in the art, a typical well logging cable has a power transmission capacity of about 1.5 KW. Using NMR pulse sequences known in the art it is impractical to increase the RF power in order to improve signal to noise or to increase the axial speed ("logging speed") at which the instrument is moved through the wellbore (the increased speed being desired by the wellbore operator to save operating time and associated costs). It is also impractical to combine NMR well logging instruments using pulse sequences known in the art with other well logging instruments because the NMR logging instrument uses nearly the entire power transmission capacity of the typical well logging cable.

SUMMARY OF THE INVENTION

The invention is a method for acquiring and processing nuclear magnetic resonance measurements of a material to increase the signal to noise ratio of the NMR signals. A modified CPMG sequence is used wherein the duration of the refocusing pulse is selected to maximize the signal to noise ratio of the pulse echo signals relative to a standard CPMG sequence wherein the refocusing pulse has a duration twice the duration of the tipping pulse.

DESCRIPTION OF THE PREFERRED EMBODIMENT

Figure 1:
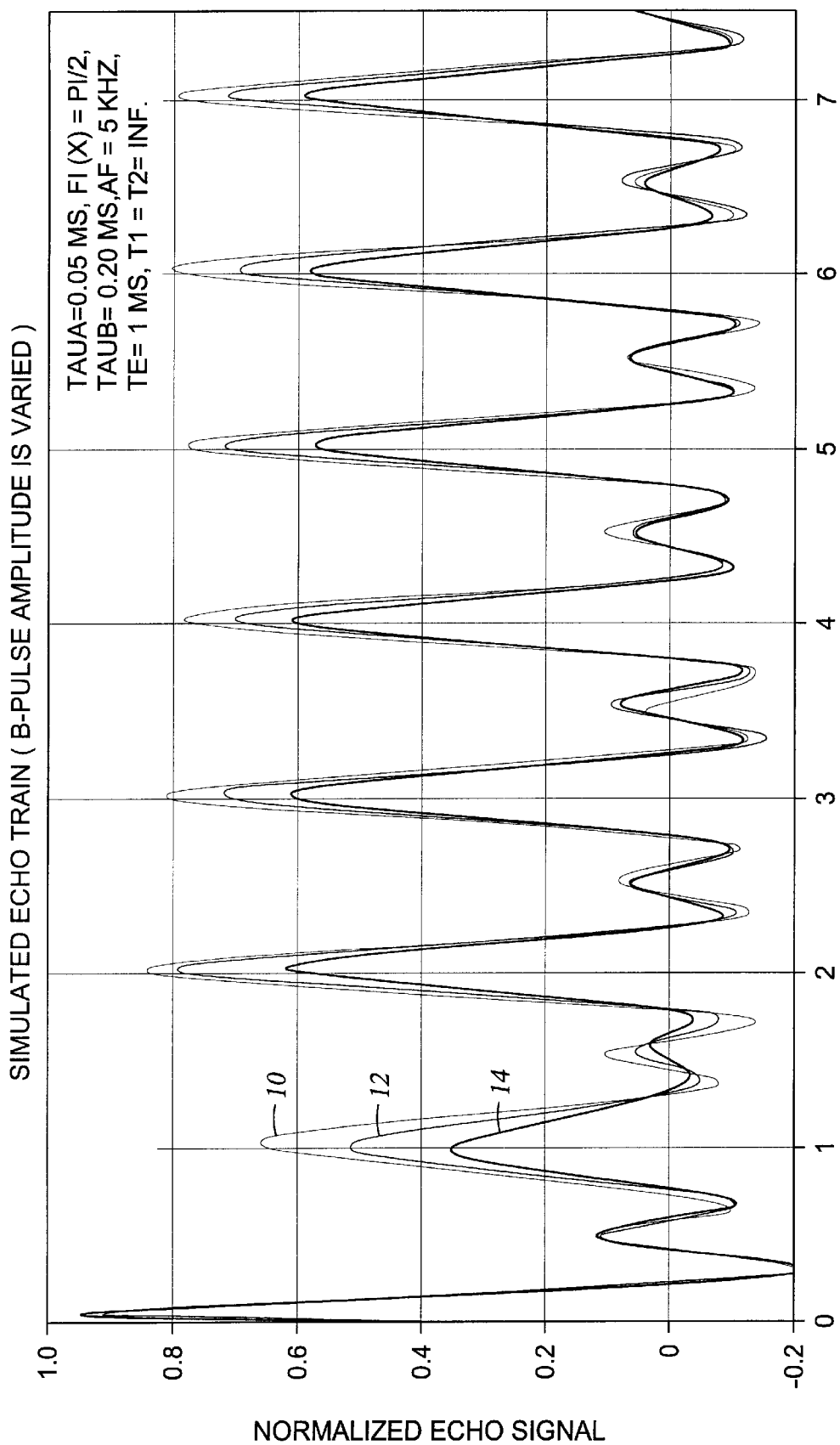
FIG. 1 shows a simulated spin echo train for B-pulse flip angles of 180°, 120° and 90° when the flip angle induced by B-pulses is selected by varying the amplitude of the B-pulses.

A typical nuclear magnetic resonance ("NMR") instrument which can make measurements according to this invention is described, for example, in U.S. Pat. No. 5,585,720 issued to Edwards, the contents of which are incorporated herein by reference. The instrument described in Edwards includes a permanent magnet for inducing a static magnetic field within the materials to be analyzed. In particular, the materials to be analyzed can include earth formations surrounding a wellbore. The instrument in Edwards includes an antenna coil which can be wound around the magnet, circuitry for applying pulses of radio-frequency (RF) power to the antenna coil, and circuitry for detecting voltages induced in the antenna coil as a result of nuclear magnetic resonance phenomena, particularly that of hydrogen nuclei present in the earth formations.

As is known in the art, the RF pulses applied to the antenna coil of NMR apparatus such as the one in Edwards typically include an initial RF pulse having a duration and amplitude which reorients the nuclear spin axes of the hydrogen nuclei in the earth formations so that they become substantially perpendicular to the direction of the static magnetic field induced by the magnet. This first RF pulse (hereafter "A-pulse") is said to induce an angular deflection of about 90° in the spin axes of the hydrogen nuclei. Later in the measurement cycle known in the art, a sequence of additional RF pulses (referred to as "B-pulses"), each of these B-pulses having a duration and amplitude selected to reorient the extant nuclear spin axes by about 180°, is then applied to the antenna coil. In between B-pulses, the antenna coil is connected to a receiver circuit to detect voltages induced in the antenna coil as the nuclear spin axes "rephase", an event called the pulse-echo or spin echo. The combination of A-pulse and 180 degree B-pulses is known as a Carr-Purcell-Meiboom-Gill (CPMG) sequence.

U.S. Pat. No. 5,023,551 issued to Kleinberg discloses an NMR pulse sequence for use in the borehole environment which combines a modified fast inversion recovery (FIR) pulse sequence with a series of more than ten, and typically hundreds, of CPMG pulses according to $$[W_i - 180t_i - 90_x - (t_{cp} - 180_y - t_{cp} - \text{echo})_j]_i \qquad (1)$$

where j=1, 2, . . . , J, and J is the number of echoes collected in a single CPMG sequence, where i =1, 2, . . . , I and I is the number of waiting times used in the pulse sequence, where $W_i$ are the recovery times before the inversion pulse, and where $t_i$ are the recovery times before a CPMG sequence, and where tc is the Carr-Purcell spacing. The phase of the RF pulses 90 and 180 is denoted by the subscripts X and Y, Y being phase shifted by $\pi/2$ radians with respect to X. The subscripts also conventionally relate to the axis about which rotation of the magnetization occurs during the RF pulse in a local Cartesian co-ordinate system centered on the nucleus in which the static magnetic field is aligned in the Z direction and the RF field in the X direction. This sequence can be used to measure both T1 and T2, but is very time consuming, limiting logging speed. If $t_{cp}$ is set to zero and the inverting pulse is omitted then the sequence defaults to standard CPMG for measuring T2 only.

The "A" pulse or the tipping pulse in a CPMG sequence is the 90° pulse in eq. (1) and the "B" pulse or the refocusing pulse in a CPMG sequence is 180°.

As is understood by those skilled in the art, the amplitude of the induced voltages from spin rephasing (pulse-echo voltages) decreases after each successive B-pulse applied to the antenna coil. The rate at which the amplitude of the successive pulse-echo voltages decays is related to properties of the earth formations such as fractional volume of pore space and the bulk volume of mobile fluids filling the pore space, as is known in the art.

In the invention, it has been determined that the B-pulses can, and preferably do, have a duration and amplitude selected to cause the nuclear spin axes to reorient by an angular deflection different from 180°. FIG. 1 shows a simulated spin echo "train" (the magnitude of the voltages induced in the receiver coil for each of the spin echoes) for B-pulse angular reorientation (hereafter referred to as the "flip" angle) of 180°, 120° and 90°, at curves 10, 12, and 14, respectively. What is apparent from FIG. 1 is that the average amplitude of the spin echoes is reduced only by about 30 percent (although the first and second echoes are reduced in amplitude substantially more than this) by reducing the flip angle of the B-pulses from 180° to 90°.

Reducing the flip angle of the B-pulses from 180° to 90°, however, reduces the amount of electrical power consumed in generating the B-pulses by about 75 percent. The reduction in electric power consumption makes possible generation of additional spin echo measurement sequences using the same overall amount of electrical power. These additional spin echo measurement sequences can be summed or "stacked" to improve the signal to noise ratio ("SNR") over that of a single CPMG sequence using 180° B-pulses, while using the same overall amount of electrical power.

For example, four spin echo trains each having a 90° flip angle B-pulses could be used, these sequences in total consuming the same overall electrical power as a single spin echo train having 90° flip angle B-pulses. The four echo trains can then be stacked. The signal to noise ratio ("SNR") of the four stacked spin echo trains would be twice (square root of four) that of a single spin echo train having 90° B-pulses. Four, stacked spin echo trains having 90° B-pulses would have SNR about 50 percent more than a single spin echo train having 180° B-pulses, owing to the amplitude reduction of the individual spin echoes of about 30 percent for 90° B-pulse spin echoes as compared to 180° B-pulse spin echoes. The 90° degree B-pulse echo trains, however, would use about the same amount of electrical power as the single, 180° B-pulse sequence. It should be noted that each spin echo train has only one A-pulse, so the A-pulse duration and amplitude do not materially affect the overall electrical power consumption because the typical spin echo train includes about 500 to 1,000 B-pulses, as is known in the art. Another example spin echo train measurement sequence can include stacking only three spin echo trains each having 90° B-pulses. This measurement technique would both reduce electrical power consumption and modestly increase overall SNR as compared to a single echo train having 180° B-pulses.

Acquiring multiple spin echo trains for summing or stacking can be done in a number of different ways. One way would be to wait for an amount of time between spin echo measurement sequences of about 5 times the T1 value, to allow nuclei in the medium surrounding the instrument to reorient along the static magnetic field. As is understood by those skilled in the art of well logging, waiting for nuclear spin reorientation along the static magnetic field would make the overall measurement technique relatively slow. Therefore, another technique for acquiring multiple measurement sequences for stacking can be performed using an instrument such as one described in U. S. Pat. No. 5,712,566 issued to Taicher et al, the contents of which are incorporated herein by reference The instrument described in Taicher et al can make NMR measurements at a plurality of different radio frequencies. Because the magnet in that instrument induces a static magnetic field having an amplitude gradient, making NMR measurements at different frequencies would cause nuclear magnetic excitation in different excitation volumes. This would eliminate the need to wait between measurement sequences since nuclear reorientation in one excitation volume would not materially affect measurements made in a different excitation volume.

In more general terms, if noise in the measurements is normally distributed, it is possible to determine an optimal flip angle, α, for the spin echo train for any given DC (average) by maximizing the value:

$$\frac{180}{\alpha} \cdot \frac{S_\alpha}{S_{180}} \tag{2}$$

where S 180 represents the SNR for the signals acquired using a conventional flip angle of $S_{180}$ and $S_\alpha$ represents the SNR for the signals acquired using a flip angle α. The foregoing description of stacking a number of echo trains to improve SNR while maintaining the same overall power usage is not the only possible way to acquire NMR measurements using the method of this invention. As previously explained, the overall amplitude (and consequently SNR) of the spin echoes in a single echo train using 90° B-pulses, for example, is reduced by about 30 percent from a spin echo train using 180° B-pulses. However, in the same example, the power used in generating the echo train using 90° B-pulses is reduced by about 75 percent from that needed to generate the echo train using 180° B-pulses. Using an expression such as that in equation (1), NMR measurements can be made using single echo trains wherein the flip angle is selected to optimize the SNR with respect to the amount of power used to generate the spin echo train. This can result in reduced power usage for a given SNR, or may also allow the system designer to use single echo train measurements wherein the power usage is minimized while maintaining an acceptable SNR for the measurements.

Figure 2:
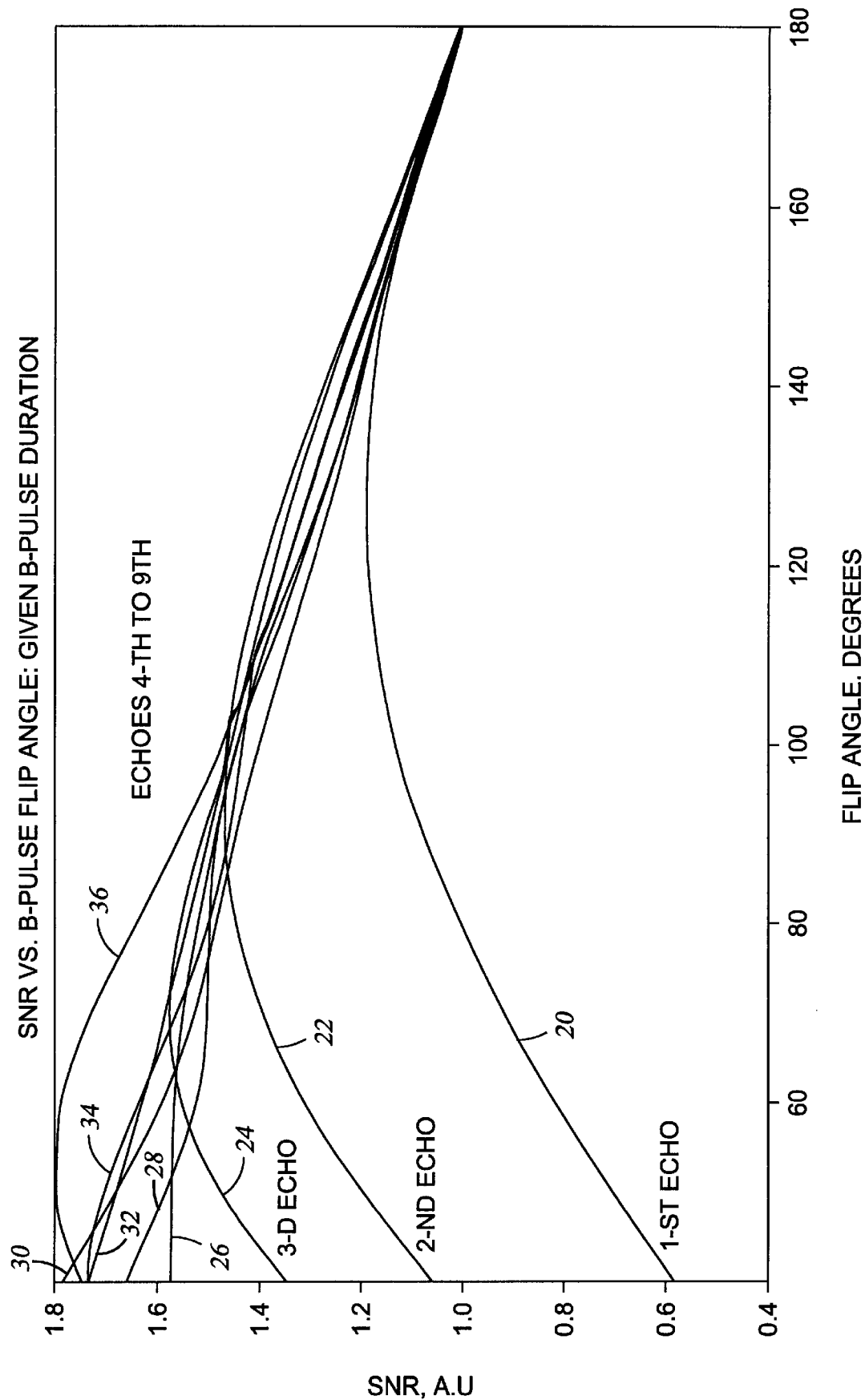
FIG. 2 shows a graph of SNR of "stacked" spin echo trains having varying B-pulse durations, but the same overall power consumption as a single 180° B-pulse spin echo train, normalized to the SNR of the single 180° B-pulse echo train.

FIG. 2 shows SNR of spin echoes in summed or "stacked" echo trains having varying B-pulse flip angles, the SNR being normalized to the SNR of a single echo train having 180° flip angle B-pulses. The number of echo trains stacked for each of the various flip angles is calculated to have the same overall DC power consumption as the single echo train having 180° B-pulses. The SNR for some of the individual spin echoes in the "stacked" echo train is shown with respect to the selected B-pulse flip angle. It should be noted that the SNR for these individual echoes represents the stacked value, where the number of these same individually indexed spin echoes in each of the echo trains is equal to the total number of echo trains which is summed. For purposes of calculating the curves shown in 90°, the number of stacked echo trains can be represented by the expression:

$$N = \sqrt{\frac{P_\alpha}{P_{180}}} \tag{3}$$

where N represents the number of stacked echo trains, $P_\alpha$ represents the power consumed by each spin echo train having B-pulses of flip angle α, and $P_{180}$ represents the power consumed by a spin echo train having 180° B-pulses. As a practical matter, however, an integral (whole) number of spin echo trains (N) for the selected B-pulse flip angle will most likely stacked for actual spin echo measurements made by a logging instrument in a wellbore.

As can be observed in FIG. 2, for the second through the ninth spin echoes, shown as curves 22 through 36, respectively, the stacked SNR is generally greater than that in a corresponding single echo train having 180° B-pulses. As a group, these individual echoes peak in stacked SNR at about 90° to 110°. The first echo, shown at curve 22, is substantially different, having stacked SNR of about 58 percent of a 180° spin echo at a flip angle of 40°, with SNR peaking at about 120° to 140°. Using a selection criterion that the stacked first spin echoes should have SNR at least equal to that of a single spin echo train using 180° flip angle B-pulses, it can be inferred that B-pulse flip angles in the range of about 80° to 120° will provide substantially improved SNR with respect to an echo train having 180° B-pulses, while having the same DC power consumption to generate the B-pulses as that needed to generate a single echo train having 180° B-pulses. It should be noted that the graph in FIG. 2 assumes that the particular B-pulse flip angle is selected by selecting the amplitude of the B-pulses. The duration of the B-pulses remains substantially constant. The converse case where the B-pulse amplitude is maintained constant and the duration is varied to select the flip angle will be further explained.

Figure 3:
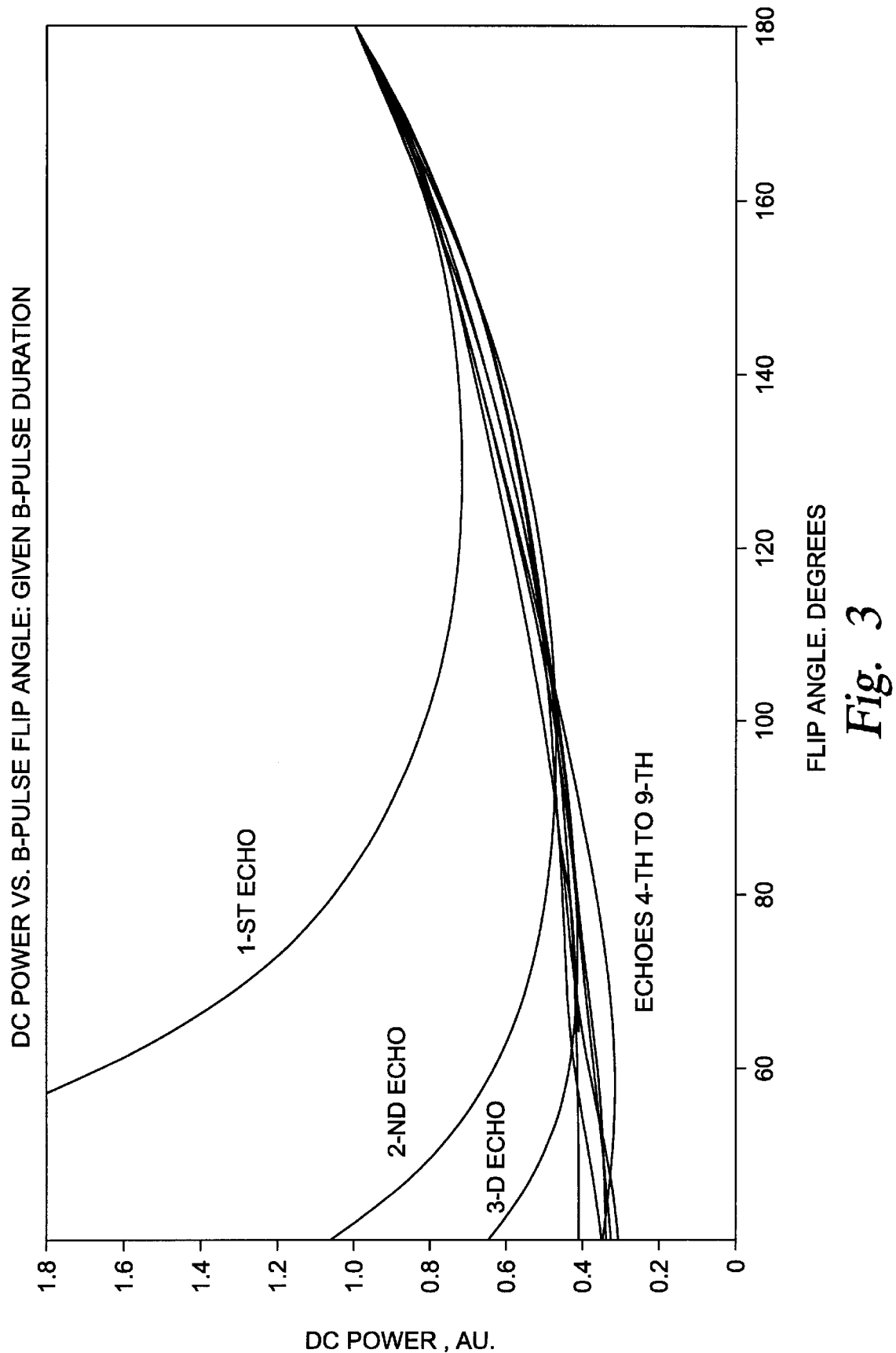
FIG. 3 shows the DC power consumption of the stacked spin echo trains having varying B-pulse durations, but the same SNR, normalized to the power consumption of a single 180° B-pulse echo train.

FIG. 3 shows the DC power consumption used in generating B-pulses having the same varying flip angles as shown in FIG. 2, normalized to the DC power consumption used for generating a single 180° B-pulse echo train, where the SNR for each of the types of spin echo trains is held substantially constant. Similarly as in the results shown in FIG. 2, for B-pulse flip angles in a range of about 80° to 120° the specific DC power consumption for generating the B-pulses is most reduced from that used to generate B-pulses having a flip angle of 180°.

Figure 4:
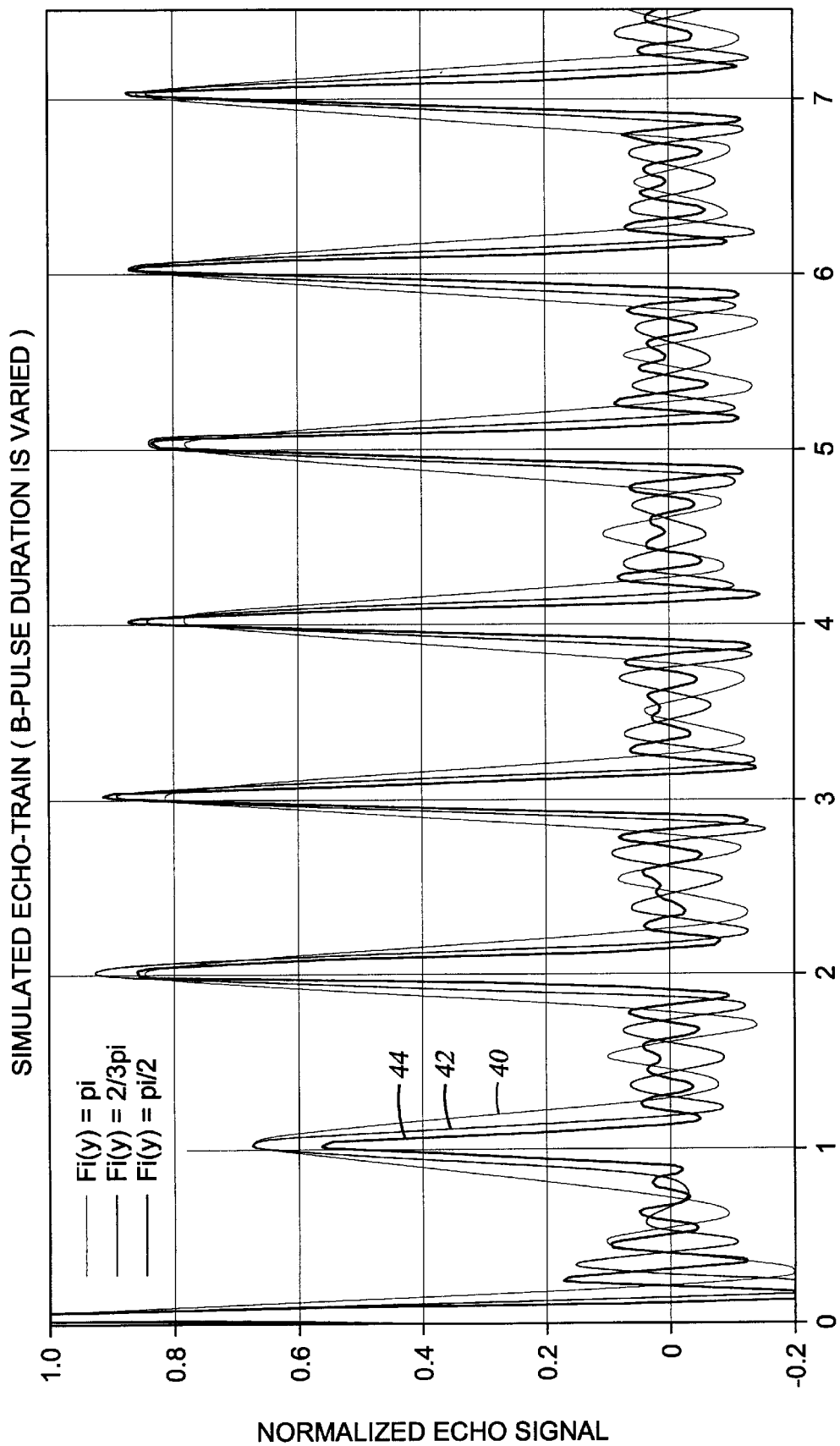
FIG. 4 shows simulated echo trains where the flip angle induced by B-pulses is selected by varying the duration of the B-pulses.
Figure 5:
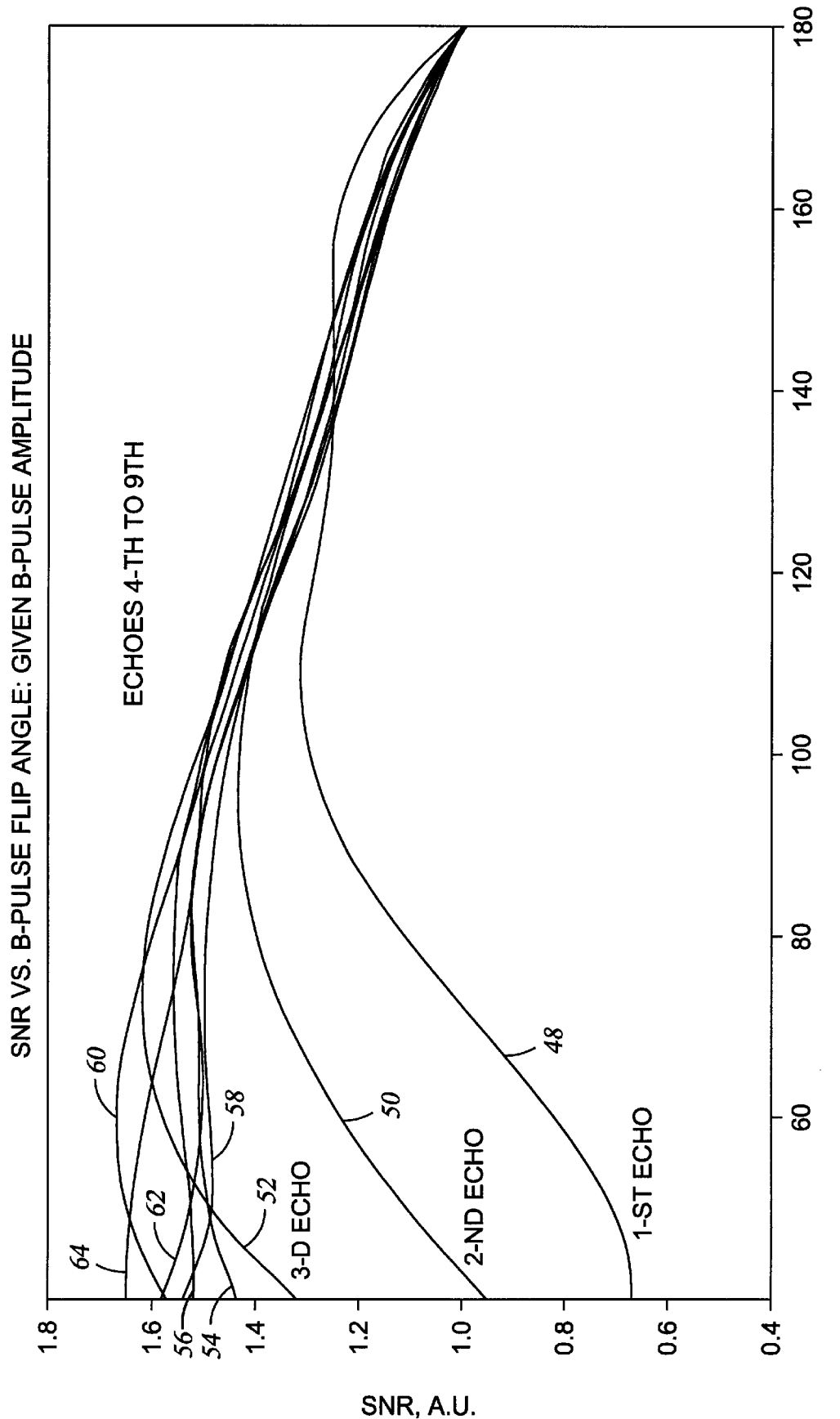
FIG. 5 shows the SNR of stacked echo trains simulated as in FIG. 4 with respect to the flip angle of the B-pulses, normalized to the SNR of a single echo train having a B-pulse flip angle of 180°.

The flip angle induced by the B-pulses can also be selected by varying the duration of the B-pulses while maintaining a substantially constant B-pulse amplitude. An echo train simulation similar to the one shown in FIG. 1 is shown in FIG. 4, where the amplitudes of spin echoes are shown for flip angles of 180°, 120° and 90° at curves 40, 42, and 44, respectively. In the simulation results shown in FIG. 5, the B-pulse flip angle is selected by adjusting the B-pulse duration while maintaining the amplitude substantially constant. Corresponding SNR curves with respect to the B-pulse flip angle are shown in FIG. 5 for the first echo at curve 50, the second echo at curve 52 and the third echo at curve 54. Fourth through ninth echoes are shown as a group of curve 56. As can be observed in FIG. 5, the SNR for the first echo 50 has a "plateau"-like maximum in a range of about 100° to 160°. The second echo 52 has a peak SNR in the range of about 95–115°. In the graph of FIG. 5, the receiver bandwidth is set to an amount corresponding to the spin echo signal spectrum. In the case of 180°, 120° and 90° pulses, this bandwidth is 5 kHz, 7.5 kHz and 10 kHz, respectively.

Figure 6:
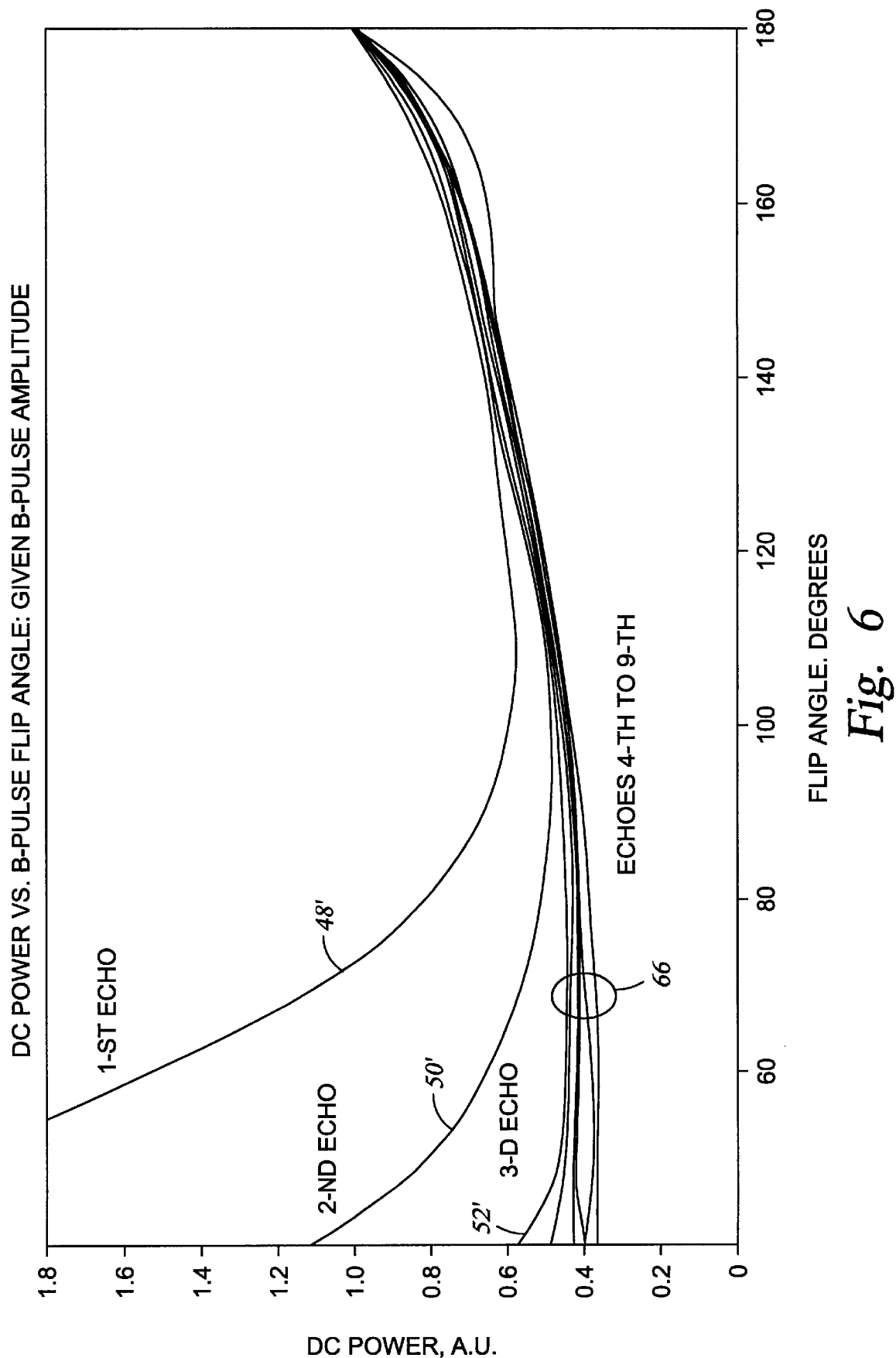
FIG. 6 shows the DC power consumption of the stacked echo trains simulated as in FIG. 4 with respect to the flip angle of the B-pulses, normalized to the DC power consumption of a single echo train having a B-pulse flip angle of 180°.

The DC power consumption normalized to that of 180° -duration B-pulses, for the simulated spin echoes shown in FIG. 4, is shown in FIG. 6. The first echo 60 has a minimum power consumption in a range of about 100° to 160°. The second echo 62 has a minimum power consumption in a range of about 95–115°.

It should be noted that reducing the B-pulse width to select the flip angle may affect the necessary width of the A-pulse. In conventional NMR spin echo measurements the B-pulses have a duration of about twice that of the A-pulses. If the B-pulse flip angle is reduced by selecting a reduced pulse duration, it may be necessary to correspondingly reduce the A-pulse width (but correspondingly increase the A-pulse amplitude to maintain a 90° flip angle) to avoid the situation where the A-pulse does not equally excite all the nuclear magnetic spins which will then be affected by the B-pulses. This effect would spoil any possible signal to noise improvement offered by the method of the invention unless the A-pulse width is reduced to approximately one-half the B-pulse width.

To summarize, using an expression similar to that of equation (1), a B-pulse flip angle can be selected for NMR spin echo measurement sequences which provides a maximum SNR while minimizing the use of electrical power by the instrument.

As is known in the art, NMR well logging measurements as a practical matter are not conducted in a perfectly homogeneous static magnetic field. The NMR signals detected by the typical well logging instrument will therefore have a non-zero bandwidth. A consequence of the bandwidth of the NMR signals is that the spin echo peak amplitudes do not precisely correspond to the theoretical spin echo amplitudes which would obtain for given earth formation properties if the static magnetic field had zero gradient. The magnitude of the effect of signal bandwidth on the spin echo amplitudes is well known. As is known in the art, a correction coefficient can be defined for each spin echo to adjust its amplitude to the theoretical value which would obtain in a zero gradient static magnetic field. This is shown by the following expression:

$$E_j^c = K_j E_j^m$$

where $E_j^c$ represents the corrected amplitude of the j-th spin echo, $K_j$ represents the j-th correction factor, and $E_j^m$ represents the j-th measured spin echo amplitude. For the typical NMR well logging instrument, a series of correction factors can be determined for each of the j spin echoes in any measurement sequence. In the case where T1=T2, the values of the correction factors $K_j$ are not dependent on T2. Therefore the same set of correction factors can be used for any set of spin echo measurements when T1=T2.

Figure 7:
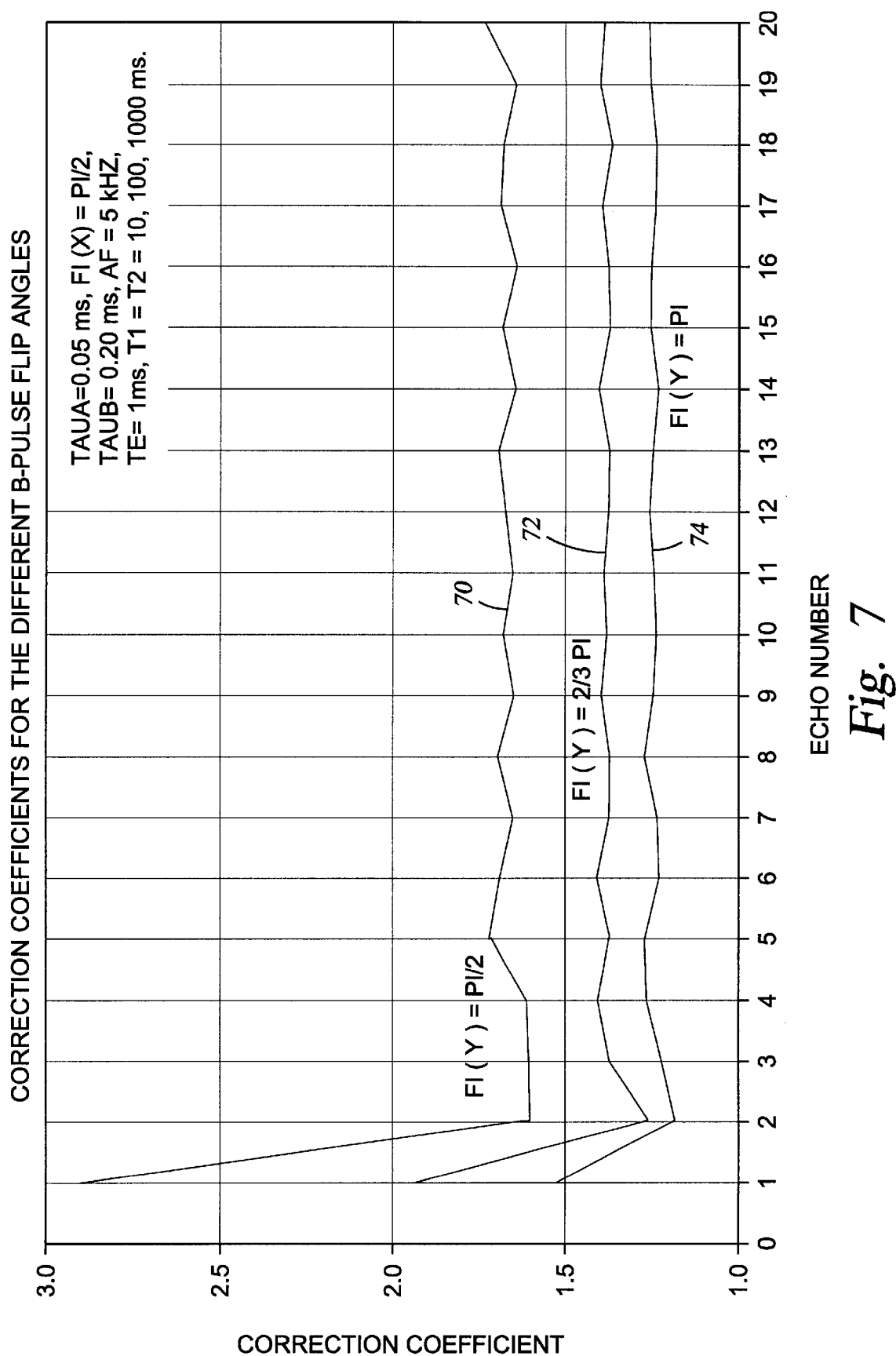
FIG. 7 shows a graph of correction coefficients for each of the first 20 echoes in an echo train for B-pulse flip angles of 180°, 120° and 90°, where the value of T2 is selected to be 10, 100 and 1,000 milliseconds for each flip angle.

It has been determined that similar correction factors can be determined for spin echoes in an echo train where the rephasing pulses (B-pulses) have a flip angle other than 90°, which type of echo train is particularly shown in this invention. Referring to FIG. 7, three sets of curves are shown, each set representing the value of the correction factor for particular spin echoes. The value of the correction factor for a B-pulse flip angle is shown in curve set 74. Curve set 74 actually represents three individual curves of correction factor with respect to echo number where the T2 (and T1) value for each individual curve in the set 74 is 10, 100 and 1,000 milliseconds. Set 74 appears as only one curve because the correction factors are essentially independent of T2. Similarly for B-pulse flip angles of 120°, shown in set 72, and 90°, shown in set 70, the values of the correction factors do not change with changes in T2.

The curve sets 70, 72, 74 in FIG. 7 suggest that a different set of correction factors must be determined for each particular value of flip angle, bandwidth and T1/T2 ratio. The values of correction factors are pre calculated just once and can be stored in look up tables, for example, for performing corrections. Therefore this invention does not require any specialized processing as compared to traditional correction procedures where the B-pulse flip angle is 180°.

Reduction of the B-pulse duration leads to an increase of excitation volume in an NMR device using a gradient magnetic field. This is due to the fact that a shorter pulse has a larger bandwidth and hence would, in a gradient field, refocus spins from a larger volume. This larger volume would lead to a larger signal level. Those versed in the art would recognize that the corresponding increase in receiver bandwidth needed to take advantage of the increased bandwidth will lead to an increase in the noise level in the receiver by a factor $\sqrt{(\Delta)}$. As a result, the increase in the signal due to the increased bandwidth may not compensate for the increased noise and the SNR will drop even though the signal level itself will go up with reduction of the refocusing pulse duration.

Figure 8:
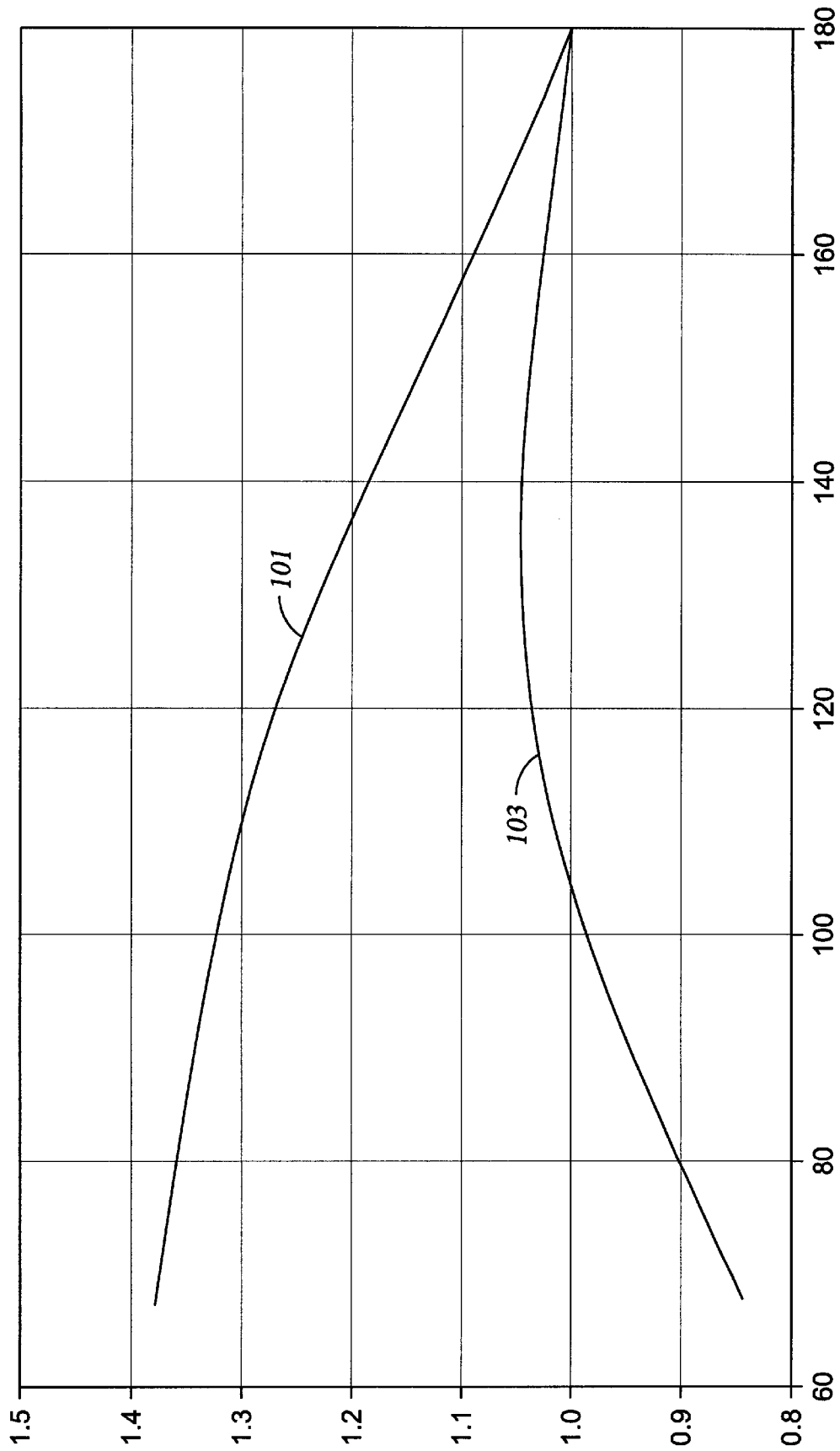
FIG. 8 shows the dependence of the pulse echo signal and the SNR of the pulse echo signal on the duration of the B-pulse.

Turning now to FIG. 8, the result of changing the duration of the refocusing pulse in a CPMG sequence are illustrated. The abscissa is the duration of the refocusing pulse expressed in terms of the flip angle in degrees. The signal level is given by 101 and, as discussed above, increases as the duration of the B-pulse is reduced. As a matter of fact, it is still increasing when the flip angle of the B-pulse is reduced to 60°. The SNR is given by 103 and, for the field configuration used in the simulation, has a maximum around 130°. For the display in FIG. 8, relaxation amplitude SNR is chosen to represent the SNR in the steady state region corresponding to pulse echo 3 or later. The simulation results shown in FIG. 3 assume, without being a limitation, no relaxation of the spins: comparable results will occur if relaxation is included in the modeling.

It is clear from the results presented in FIG. 8 that the reduction of the flip angle of the B-pulse to 130° increases SNR by about 5% compared to prior art CPMG sequences with a 180° refocusing pulse with a reduction in DC power consumption by about 30% since the DC power consumption is proportional to the duration of the refocusing pulse when its amplitude is held constant. By reducing the refocusing pulse to 90°, the power consumption is reduced by 50% with only a 5% drop in SNR.

The discussion about improved signal level with reduced duration of the B-pulse is valid if and only if the spectrum of the A-pulse is broader than the spectrum of the B-pulse: the B-pulse cannot refocus spins that have never been tipped in the first place. Hence in a preferred embodiment of the invention, the B-pulse duration should be between about 1.3–2.0 times the A pulse duration while maintaining the A pulse amplitude to maintain a 90° rotation angle.

Those skilled in the art will devise other embodiments of this invention which do not depart from the spirit of the invention as disclosed herein. Accordingly, the invention should be limited in scope only by the attached claims.

What is claimed is:

1. A method for determining a parameter of interest of a volume of earth formation with a borehole tool conveyed in a borehole within the formation, the method comprising:

(a) using a magnet assembly on the borehole tool for producing a static magnetic field having a field strength within predetermined limits in said volume of the formation and aligning nuclear spins within said volume parallel to a direction of the static field;

b) producing a radio frequency (RF) magnetic field in said volume of the formation, said RF magnetic field having a direction substantially orthogonal to a direction of the static field, the RF field including a pulse sequence:

$$W-T-t_s-R-(t_{cp}-\text{echo}-t_{cp}-R)_j$$

wherein W is a wait period, T is a tipping pulse for tipping the nuclear spins at an angle substantially equal to ninety degrees to cause precession thereof, $t_s$ is a waiting time, $t_{CP}$ is the Carr-Purcell time, R is a refocusing pulse, j=1, 2, . . . J, and J is the number of echoes collected in a single sequence of pulses;

(c) measuring with a receiver coil on the borehole tool nuclear magnetic resonance signals induced by the pulsed RE field in the formation; and (d) processing said measured signals to determine the parameter of interest; wherein the refocusing pulse has a duration selected to increase a signal to noise ratio (SNR) of said signals relative to a refocusing pulse having twice the duration of the tipping pulse;

wherein processing said measured signals further comprises determining correction coefficients for correcting amplitudes of said spin echo signals to a theoretical value which would be obtained in a zero gradient static magnetic field.

2. The method of claim 1 wherein a ratio of said duration of the refocusing pulse to a duration of the tipping pulse has a value between 1.3 and 20.

3. The method of claim 1 wherein, when a transverse relaxation time of said formation equals a longitudinal relaxation time of said formation, said correction coefficients are independent of said transverse relaxation time.

* * * * *